United States Patent
Okamoto

(10) Patent No.: US 9,077,276 B2
(45) Date of Patent: Jul. 7, 2015

(54) MOTOR CONTROL METHOD AND MOTOR CONTROL APPARATUS FOR DENTAL HANDPIECE

(75) Inventor: Hideki Okamoto, Tochigi (JP)

(73) Assignee: NAKANISHI INC., Tochigi (JP)

( * ) Notice: Subject to any disclaimer, the term of this patent is extended or adjusted under 35 U.S.C. 154(b) by 7 days.

(21) Appl. No.: 13/376,447

(22) PCT Filed: May 18, 2011

(86) PCT No.: PCT/JP2011/002763
§ 371 (c)(1),
(2), (4) Date: Dec. 6, 2011

(87) PCT Pub. No.: WO2012/001869
PCT Pub. Date: Jan. 5, 2012

(65) Prior Publication Data
US 2013/0099710 A1   Apr. 25, 2013

(30) Foreign Application Priority Data
Jul. 2, 2010 (JP) ................. 2010-151846

(51) Int. Cl.
| | |
|---|---|
| H02P 29/02 | (2006.01) |
| H02P 7/06 | (2006.01) |
| A61C 1/06 | (2006.01) |
| A61C 1/00 | (2006.01) |
| A61C 1/18 | (2006.01) |
| H02P 7/18 | (2006.01) |
| H02P 7/288 | (2006.01) |

(52) U.S. Cl.
CPC ............ *H02P 29/027* (2013.01); *A61C 1/0015* (2013.01); *A61C 1/06* (2013.01); *A61C 1/186* (2013.01)

(58) Field of Classification Search
CPC ...................................................... H02P 23/04
USPC .............. 433/98, 118, 224, 27, 99, 122, 131, 433/116, 103, 102
See application file for complete search history.

(56) References Cited

U.S. PATENT DOCUMENTS

| | | | | |
|---|---|---|---|---|
| 4,792,735 | A * | 12/1988 | Kim ............................. | 388/821 |
| 5,543,695 | A * | 8/1996 | Culp et al. .................... | 318/432 |
| 5,947,729 | A * | 9/1999 | Bell ............................. | 433/98 |
| 5,980,248 | A * | 11/1999 | Kusakabe et al. ............. | 433/27 |
| 6,017,354 | A | 1/2000 | Culp et al. | |
| 6,229,278 | B1 * | 5/2001 | Garces et al. ................ | 318/801 |
| 6,616,446 | B1 * | 9/2003 | Schmid ......................... | 433/27 |
| 6,929,476 | B2 * | 8/2005 | Katsuda et al. ............... | 433/98 |

(Continued)

FOREIGN PATENT DOCUMENTS

| | | |
|---|---|---|
| CN | 1186378 A | 7/1998 |
| CN | 2619594 Y | 6/2004 |

(Continued)

*Primary Examiner* — Eduardo Colon Santana
*Assistant Examiner* — Said Bouziane
(74) *Attorney, Agent, or Firm* — Pearne & Gordon LLP

(57) ABSTRACT

The present invention relates to a motor control method for a dental handpiece provided with a motor that rotationally drives a cutting tool. The control method includes a step A of limiting the motor current to a first limit current I1 when the load torque applied to the cutting tool exceeds a preset limit torque value, and a step B of controlling the motor current to be equal to or lower than a second limit current, which is lower than the first limit current, when it is detected that the motor stops rotating.

8 Claims, 5 Drawing Sheets

(56) References Cited

U.S. PATENT DOCUMENTS

2002/0064756 A1* 5/2002 Pagnini et al. ............... 433/102
2008/0203964 A1* 8/2008 Koike .......................... 318/799

FOREIGN PATENT DOCUMENTS

| | | |
|---|---|---|
| CN | 101355915 A | 1/2009 |
| DE | 19628854 A1 | 7/1996 |
| JP | 03-047249 A | 2/1991 |
| JP | 08-308858 A | 11/1996 |
| JP | 09-038108 A | 2/1997 |
| JP | 2001-500031 A | 9/2001 |
| JP | 3264607 B2 | 12/2001 |
| JP | 2003-019143 A | 1/2003 |

\* cited by examiner

MOTOR CONTROL METHOD AND MOTOR CONTROL APPARATUS FOR DENTAL HANDPIECE

BACKGROUND OF THE INVENTION

1. Field of the Invention

The present invention relates to a motor control method and a motor control apparatus for a dental handpiece that cuts teeth or forms a root canal with a cutting tool.

2. Description of the Related Art

To cut teeth or form a root canal, a dental handpiece provided with an electrical motor as a driving source is used. The operator selects one suitable for the operation from among a plurality of types of cutting tools.

A known method of controlling the motor of such a dental handpiece is a feedback control, in which the motor is controlled so as to keep the preset rotational speed by detecting the rotational speed of the motor and increasing or decreasing the motor driving voltage based on the detected rotational speed.

If the load torque on the cutting tool increases and the rotational speed decreases, a motor control apparatus based on the feedback control increases the motor driving voltage, thereby restoring the preset rotational speed.

However, when the feedback control is used for root canal formation or other operations that involve using a thin cutting tool that is easily broken, there arises an operational problem that an excessive torque can be applied to the cutting tool, and the cutting tool can be broken or jammed into a root canal.

To solve such a problem, the motor control apparatus proposed in Japanese Patent No. 3264607 does not perform the feedback control but controls the motor output characteristics so as to decrease the rotational speed as the load torque applied to the cutting tool increases. When the load torque on the cutting tool reaches a preset reference torque, the motor control apparatus performs one of three operations: (1) to decrease the rotational speed of the motor, (2) to stop the motor, and (3) to reverse the rotation of the motor.

In this way, the motor control apparatus according to Japanese Patent No. 3264607 can prevent the cutting tool from being broken and can remove the cutting tool from the root canal by reversing the rotation of the motor, and thus, the operability is improved.

However, although the motor control apparatus disclosed in Japanese Patent No. 3264607 can prevent the cutting tool from being broken or jammed into a root canal, the motor control apparatus is inferior to the feedback control in cutting efficiency because the rotational speed of the cutting tool decreases as the load torque increases.

In addition, in the above-described case (2) where the motor is stopped, the rotation of the motor is stopped by stopping application of the driving voltage to the motor as shown in the diagrams (a) and (b) in FIG. 5 of Japanese Patent No. 3264607. As a result, the torque of the motor (the cutting tool) in the direction of rotation suddenly drops, thereby causing a shock (referred to as discomfort hereinafter) to the patient and the operator.

In the above-described case (3) where the rotation of the motor is reversed, the driving voltage to the motor is stopped to stop the rotation of the motor before the reversal, so that the discomfort occurs as in the case (2) described above.

The present invention has been accomplished in view of such problems, and an object of the present invention is to provide a motor control method and a motor control apparatus for a dental handpiece that can prevent a cutting tool from being broken, allow efficient cutting and reduce a discomfort to a patient and an operator during operation.

SUMMARY OF THE INVENTION

The present invention relates to a motor control method for a dental handpiece, the dental handpiece having a motor that rotationally drives a cutting tool, the motor control method comprising: a step A of limiting a motor current flowing through the motor to a first limit current when a load torque applied to the cutting tool exceeds a preset limit torque value; and a step B of controlling the motor current to be equal to or lower than a second limit current, which is lower than the first limit current, when it is detected that the motor stops rotating.

According to the control method according to the present invention, the motor current is limited to the first limit current. Thereby, the rotation of the motor (the cutting tool) can be stopped (the number of rotations can be brought to 0) when the load torque applied to the cutting tool increases, and it enables to prevent the cutting tool from being broken. In addition, even when the rotation of the motor is stopped, the first limit current is still being applied to the motor, so that no torque drop (sudden decrease of the torque) occurs. When it is detected that the rotation of the motor is stopped, the motor current is controlled to be equal to or lower than the second limit current that is lower than the first limit current, so that no torque drop occurs while the load torque decreases.

Once the motor current is controlled to be equal to or lower than the second limit current, the control method according to the present invention can proceed in any of the following three modes.

A first mode is to stop power supply to the motor when the motor current becomes equal to or lower than the second limit current in the step B. This mode is used when the operation is not resumed after the rotation of the motor is stopped.

A second mode is to make the motor rotate in a reverse direction when the motor current becomes equal to or lower than the second limit current in the step B. This mode is used when the cutting tool jammed into a root canal needs to be removed from the root canal by reversing the rotation of the cutting tool.

A third mode is to make the motor rotate in a reverse direction and then rotate in a forward direction, which is the direction in which the motor rotates before it is made to rotate in the reverse direction, when the motor current becomes equal to or lower than the second limit current in the step B. This mode is used when the operation is resumed after the cutting tool jammed into a root canal is removed from the root canal by reversing the rotation of the cutting tool.

The present invention also provides a control apparatus that performs the control method described above.

A control apparatus according to the present invention comprises: a load torque detecting section that detects a load torque applied to a cutting tool; a rotational speed detecting section that detects a rotational speed of a motor; and a control section that controls the rotational speed and a motor current of the motor.

The control section controls the motor current based on the load torque detected by the load torque detecting section as described below.

That is, the control section limits the motor current to the first limit current when the load torque exceeds a preset limit torque value.

In addition, the control section controls the motor current to be equal to or lower than the second limit current that is lower than the first limit current when the load torque exceeds the limit torque value, and the rotational speed detecting section detects that the motor stops rotating.

The control apparatus according to the present invention prevents the cutting tool from being broken by limiting the motor current to the first limit current. In addition, when it is detected that the rotation of the motor is stopped, the motor current is controlled to be equal to or lower than the second limit current lower than the first limit current, and the load torque is reduced, so that the torque drop can be alleviated.

Once the motor current is controlled to be equal to or lower than the second limit current, the control apparatus according to the present invention can operate in any of the following three modes.

A first mode is to stop power supply to the motor when the motor current becomes equal to or lower than the second limit current.

A second mode is to make the motor rotate in a reverse direction when the motor current becomes equal to or lower than the second limit current.

A third mode is to make the motor rotate in a reverse direction and then rotate in a forward direction, which is the direction in which the motor rotates before it is made to rotate in the reverse direction, when the motor current becomes equal to or lower than the second limit current.

The motor control method according to the present invention controls the operation of the motor by monitoring the load torque to prevent an excessive load torque from being applied to the cutting tool and therefore can prevent the cutting tool from being broken.

The motor control method according to the present invention does not suddenly stops the motor current but gradually reduces the motor current to zero after the rotation of the motor is stopped when the load torque applied to the cutting tool exceeds the limit torque value. Therefore, the torque can be gradually reduced in the process, so that the discomfort to the patient and the operator due to the torque drop can be reduced.

DETAILED DESCRIPTION OF THE PREFERRED EMBODIMENT

In the following, the present invention will be described in detail with regard to an embodiment shown in the accompanying drawings.

Figure 1:
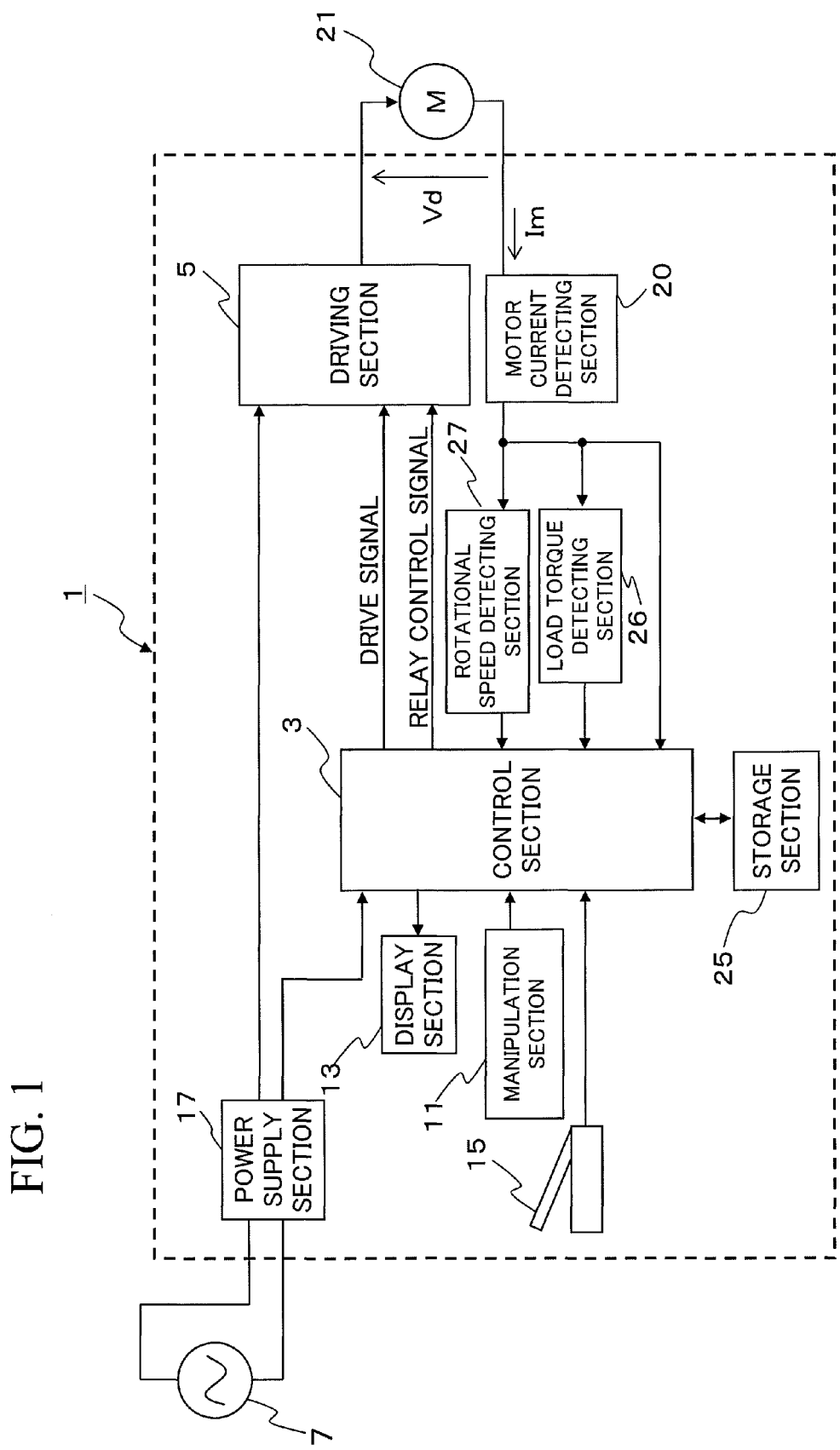
FIG. 1 is a functional block diagram showing a configuration of a motor control apparatus.

A motor control apparatus 1 according to the embodiment shown in FIG. 1 controls a motor 21, which is a three-phase brushless motor incorporated in a dental handpiece. The motor control apparatus 1 comprises a control section 3, a storage section 25, a driving section 5, a manipulation section 11, a display section 13, a foot pedal 15, a motor current detecting section 20, a rotational speed detecting section 27, a load torque detecting section 26, and a power supply section 17.

According to this embodiment, the motor 21 is driven by a pulse width modulation (PWM) driving scheme, and a PWM signal generated by the control section 3 controls the driving section 5 to supply a driving voltage to the motor 21.

In the following description, the direction of rotation of the motor 21 to cut teeth will be referred to as a forward direction, and the opposite direction will be referred to as a reverse direction.

In the following, the components will be specifically described.

<Control Section 3>

The control section 3 controls the motor 21 by comparing detection values of the rotational speed Rr of the motor 21, the load torque Tr on the motor 21 and the motor current Im of the motor 21 with driving conditions stored in the storage section 25 and generating a PWM signal in such a manner that predetermined rotational speed Rr and motor current Im are achieved. The control section 3 also controls the direction of rotation of the motor 21, the forward direction or the reverse direction.

<Storage Section 25>

The storage section 25 stores a program for the control section 3 to control the motor 21 and conditions required for controlling the driving of the motor 21 including a first limit rotational speed R1, which is the maximum rotational speed of the motor 21 rotating in the forward direction, a second limit rotational speed R2, which is the maximum rotational speed of the motor 21 rotating in the reverse direction, a limit torque T1, a first limit current I1, and a second limit current I2.

Of these driving conditions, the first limit rotational speed R1, the second limit rotational speed R2, the limit torque T1 and the second limit current I2 can be set at any value by the operator depending on what type of operation is performed, what type of cutting tool is used or the like.

As the first limit current I1, a motor current of the motor 21 corresponding to the set limit torque T1 is set.

The storage section 25 further stores driving programs for two types of cutting modes: a stop mode and a reverse mode. The driving program for the stop mode is designed to stop power supply to the motor 21 when the rotational speed or the like of the motor 21 rotating in the forward direction meets a predetermined condition. The driving program for the reverse mode is designed to make the motor 21 rotate in the reverse direction when the rotational speed or the like of the motor 21 rotating in the forward direction meets a predetermined condition. The conditions will be described in detail later with regard to the control method in each mode.

<Motor Current Detecting Section 20>

The motor current detecting section 20 has a current detecting resistor (not shown) and converts the motor current Im flowing through the motor 21 into a voltage.

<Rotational Speed Detecting Section 27>

The rotational speed detecting section 27 estimates the induced voltage of the motor 21 from the voltage value provided by the motor current detecting section 20 and determines the rotational speed Rr of the motor 21 from the induced voltage.

<Load Torque Detecting Section 26>

The load torque detecting section 26 determines the load torque Tr from the voltage value obtained by the motor current detecting section 20 based on the proportional relationship between the motor current Im and the load torque Tr.

<Manipulation Section 11>

The manipulation section 11 has a plurality of setting buttons (not shown) and a selection button (not shown).

The operator uses the setting buttons to set the driving conditions required for controlling the motor 21 including the first limit rotational speed R1, the second limit rotational speed R2, the limit torque T1, and mode selection.

The selection button is used to select the displayed information on the display section 13 and the cutting mode.

The term "display information" herein refers to settings of the driving conditions, the rotational speed Rr and the load torque Tr of the motor 21 during driving, or the like.

<Driving Section 5>

The driving section 5 has an inverter circuit formed by six field effect transistors (FET). Based on the PWM signal from a PWM signal generating circuit in the control section 3, turning on/off of the FETs are individually controlled to apply a driving voltage Vd to the motor 21.

The rotational speed Rr of the motor 21 depends on the duty ratio (duty cycle) of the PWM signal, which is the ratio of the ON period to one period of the PWM signal. If the duty ratio increases, the effective value of the driving voltage Vd applied to the motor 21 increases, and therefore, the rotational speed Rr increases. To the contrary, if the duty ratio decreases, the rotational speed Rr decreases.

If the load torque Tr on the cutting tool increases, the rotational speed Rr of the motor 21 decreases. This phenomenon can also be addressed by increasing the duty ratio of the PWM signal to increase the effective value of the driving voltage Vd. Then, the driving torque increases as the motor current Im of the motor 21 increases, resulting in an increase of the rotational speed Rr.

As described above, the motor control apparatus 1 according to this embodiment can control the motor 21 to rotate at the desired rotational speed Rr by controlling the duty ratio of the PWM signal.

The driving section 5 also has a relay (not shown) at the output part to the motor 21, and the control section 3 controls the relay to control the direction of rotation of the motor 21, the forward direction or the reverse direction.

<Display Section 13>

The display section 13 displays the rotational speed Rr, the load torque Tr and the like of the motor 21 during operation, in addition to the various driving conditions stored in the storage section 25. The display section may display the driving conditions as numerical values or in the form of a graph to improve visual comprehensibility.

<Foot Pedal 15>

The foot pedal 15 is used to control turning on/off of the rotation of the motor 21. The control section 3 detects the presence or absence of a signal from the foot pedal 15 and activates the motor 21 under the driving conditions if there is a signal from the foot pedal 15.

<Power Supply Section 17>

The power supply section 17 rectifies and transforms an alternating-current voltage from an alternating-current power supply 7 and applies a desired direct-current voltage to the control section 3 and the driving section 5.

Next, the stop mode and the reverse mode of the motor control method according to this embodiment will be described in detail.

[Stop Mode]

<Flow of Control in Stop Mode>

A procedure in the stop mode according to this embodiment will be described with reference to FIG. 2.

When the operator steps on the foot pedal 15, the motor control apparatus 1 starts to rotate the motor 21 in the forward direction (Step S101).

The control section 3 compares the load torque Tr of the motor 21 with the limit torque T1 (Step S103).

If the comparison in Step S103 shows that the load torque Tr is lower than the limit torque T1 (if NO in Step S103), the rotational speed of the motor 21 is controlled to be the limit rotational speed R1. This control is performed as follows.

A difference between the rotational speed Rr and the first limit rotational speed R1, i.e., (Rr−R1) is obtained (Step S105).

In the case where the difference is greater than 0 (if the difference>0 in Step S105), the control section 3 decreases the driving voltage Vd applied to the motor 21 in order to decrease the rotational speed Rr (Step S107). Since the motor control apparatus according to this embodiment uses the PWM driving scheme as described above, "to decrease the driving voltage Vd" herein means to decrease the duty ratio of the PWM signal. The same holds true for the other cases described below.

In the case where the difference is 0 (if the difference=0 in Step S105), the control section 3 maintains the driving voltage Vd applied to the motor 21 in order to maintain the rotational speed Rr (Step S109).

In the case where the difference is smaller than 0 (if the difference<0 in Step S105), the control section 3 increases the driving voltage Vd applied to the motor 21 in order to increase the rotational speed Rr (Step S111).

As described above, the control section 3 controls the rotational speed Rr of the motor 21 to be the first limit rotational speed R1.

Following the processing in Step S107, S109 or S111, the procedure returns to the determination in Step S103.

As described above, the motor control apparatus 1 according to this embodiment controls the rotational speed of the motor 21 by feedback control. As cutting proceeds, the load torque Tr increases. According to this embodiment, the rotational speed Rr of the motor 21 is controlled to agree with the first limit rotational speed R1 until the load torque Tr reaches the limit torque T1. Therefore, the motor control apparatus 1 can achieve high cutting efficiency.

Next, the case where the load torque Tr is higher than the limit torque T1 during feedback control will be described.

If the determination in Step S103 shows that the load torque Tr is higher than the limit torque T1 (if YES in Step S103), the motor current Im is controlled to be the first limit current I1. This control is performed as follows.

A difference between the motor current Im and the first limit current I1, i.e., (Im−I1) is obtained (Step S121).

In the case where the difference is greater than 0 (if the difference>0 in Step S121), the control section 3 decreases the driving voltage Vd applied to the motor 21 in order to decrease the motor current Im (Step S123).

In the case where the difference is 0 (if the difference=0 in Step S121), the control section 3 maintains the driving voltage Vd applied to the motor 21 in order to maintain the motor current Im (Step S125).

In the case where the difference is smaller than 0 (if the difference<0 in Step S121), the control section 3 increases the driving voltage Vd applied to the motor 21 in order to increase the motor current Im (Step S127).

As described above, the control section 3 controls the motor current Im to be maintained at the first limit current I1.

Following the processing in Step S123, S125 or S127, it is determined whether or not the motor 21 (the cutting tool) stops, that is, whether the rotational speed Rr is 0 or not (Step S129). If it is determined that the rotational speed Rr is not 0, that is, the motor 21 is still rotating (if NO in Step S129), the procedure returns to Step S103, and the processings in Step S103 and the following steps are performed. When the procedure returns to Step S103, even if the operator interrupts the operation and removes the cutting tool from the root canal to produce a no-load condition, the motor 21 generates no heat because the rotational speed Rr of the motor 21 does not exceed the first limit rotational speed R1.

If it is determined in Step S129 that the rotational speed Rr of the motor 21 is 0, that is, the motor 21 has already stopped (if YES in Step S129), a processing of decreasing the motor current Im to the second limit current I2 or lower is performed as follows. This processing is performed by decreasing the driving voltage Vd (The duty ratio of the PWM signal).

The motor current Im is compared with the second limit current I2 (Step S131).

In the case where the motor current Im is higher than the second limit current I2 (if NO in Step S131), the driving voltage Vd applied to the motor 21 is decreased to decrease the motor current Im (Step S133). If the determination in Step S131 shows that the motor current Im is equal to or lower than the second limit current I2 (if YES in Step S131), application of the driving voltage Vd is stopped to stop power supply to the motor 21 (Step S135).

The stop mode of the control method performed by the motor control apparatus 1 according to this embodiment has been described above. If application of the driving voltage Vd to the motor 21 is stopped to eliminate the motor current Im when the rotational speed Rr of the motor 21 becomes 0 (the motor 21 stops rotating), the patient and the operator feels a torque drop. However, according to this embodiment, power supply to the motor 21 is stopped after the motor current Im decreases from the first limit current I1 to the second limit current I2 or lower. If the motor current Im is gradually decreased from the first limit current I1 to the second limit current I2 in the period after the motor 21 stops rotating and before power supply to the motor 21 is stopped, the patient and the operator feels no torque drop.

If the operator steps on the foot pedal 15 again after power supply to the motor 21 is stopped, the control section 3 resumes the procedure from Step S103.

<Control Characteristics of Stop Mode>

Figure 2:
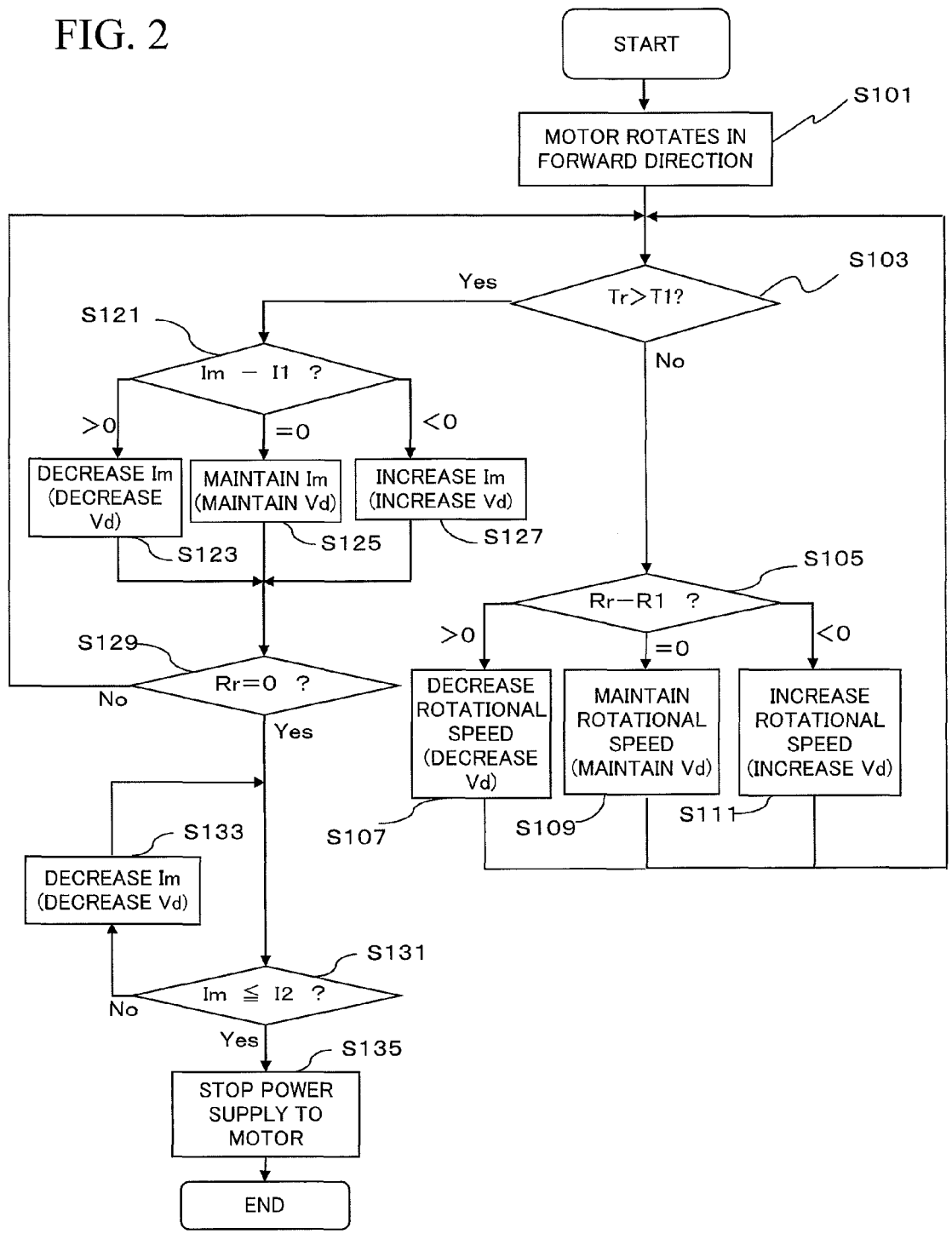
FIG. 2 is a flow chart showing a control procedure in a stop mode of a motor control method according to the present invention.
Figure 3:
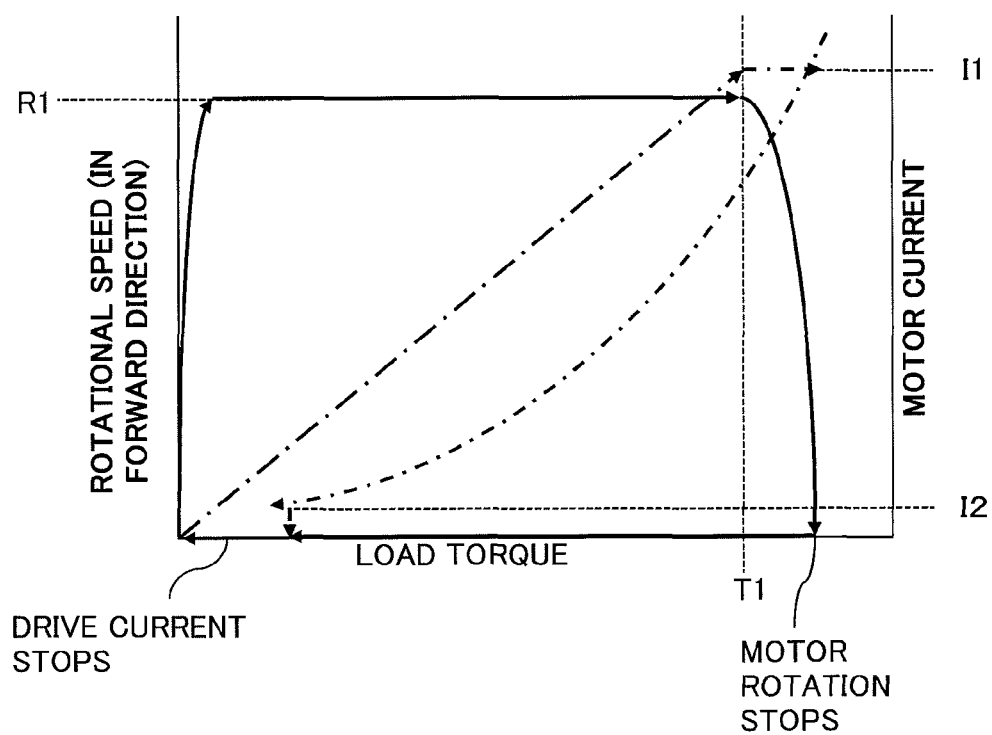
FIG. 3 is a control characteristics diagram of a load torque in the stop mode of the motor control method according to the present invention.

FIG. 3 is a diagram showing control characteristics in the stop mode shown in FIG. 2 according to this embodiment of the present invention. In FIG. 3, the left ordinate indicates the rotational speed Rr of the motor 21, the right ordinate indicates the motor current Im of the motor 21, and the abscissa indicates the load torque Tr of the motor 21.

The motor 21 rotates in the forward direction, and the rotational speed Rr of the motor 21 increases to the first limit rotational speed R1.

When the rotational speed Rr of the motor 21 reaches the first limit rotational speed R1, the feedback control is performed to maintain the rotational speed Rr at the first limit rotational speed R1.

The load torque Tr applied to the cutting tool increases as cutting proceeds. The rotational speed Rr is maintained at the first limit rotational speed R1 until the load torque Tr reaches the limit torque T1, and once the load torque Tr reaches the limit torque T1, the motor current Im is maintained at the first limit current I1.

When the load torque Tr applied to the cutting tool increases and the driving torque of the motor 21 fails to overcome the load torque Tr, the motor 21 stops rotating.

If the motor control apparatus 1 detects that the motor 21 stops rotating, the motor control apparatus 1 decreases the driving voltage Vd of the motor 21 (the duty ratio of the PWM signal) until the motor current Im becomes equal to or lower than the second limit current I2, and stops power supply to the motor 21 when the motor current Im becomes equal to or lower than the second limit current I2.

According to this embodiment, since the feedback control is performed so that the limit torque T1 is not exceeded as described above, the cutting tool can be prevented from being broken, and the operation can be efficiently performed.

In addition, according to this embodiment, when the load torque Tr reaches the limit torque T1, application of the driving voltage Vd to the motor 21 is not suddenly stopped but stopped by gradually decreasing power supply to the motor 21. As a result, the discomfort felt by the patient and the operator can be reduced.

According to the findings of the inventor, to reduce the discomfort, the second limit current I2 is preferably a fifth, more preferably a seventh, or most preferably a tenth of the first limit current I1.

[Reverse Mode]

<Control Flow in Reverse Mode>

Next, the reverse mode will be described with reference to FIG. 4.

Figure 4:
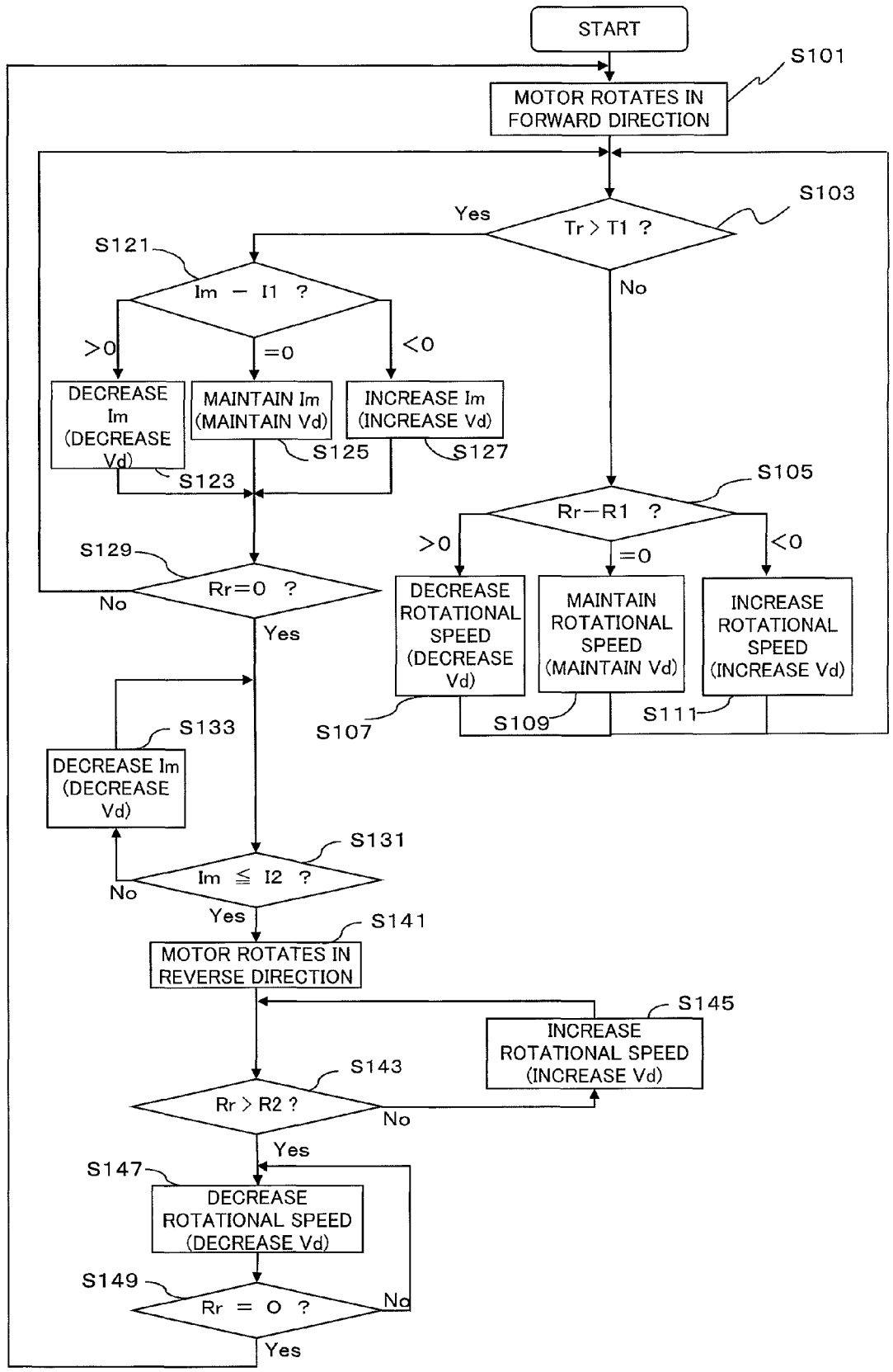
FIG. 4 is a flow chart showing a control procedure in a reverse mode of the motor control method according to the present invention.

Steps S101 to S133 shown in FIG. 4 are the same as those in the stop mode shown in FIG. 2, and therefore, only the subsequent steps will be described.

If it is determined in Step S131 that the motor current Im is equal to or lower than the second limit current I2 (if YES in Step S131), the control section 3 makes the motor 21 rotate in the reverse direction (Step S141).

When the motor 21 starts rotating in the reverse direction, it is determined whether or not the rotational speed Rr of the motor 21 reaches the second limit rotational speed R2 (Step S143).

If it is determined in Step S143 that the rotational speed Rr of the motor 21 is equal to or lower than the second limit rotational speed R2 (if NO in Step S143), the control section 3 increases the driving voltage Vd applied to the motor 21 in order to increase the rotational speed Rr (Step S145), and makes the determination in Step S143 again.

That is, the driving voltage Vd applied to the motor 21 is gradually increased until the rotational speed Rr of the motor 21 exceeds the second limit rotational speed R2.

If it is determined in Step S143 that the rotational speed Rr of the motor 21 exceeds the second limit rotational speed R2 (if YES in Step S143), the control section 3 decreases the driving voltage Vd applied to the motor 21 in order to decrease the rotational speed Rr of the motor 21 (Step S147).

The determination in Step S143 is to determine whether the cutting tool is removed from the root canal based on the rotational speed Rr of the motor 21. Therefore, the rotational speed Rr under the no-load condition when the operator has removed the cutting tool from the root canal is set as the second limit rotational speed R2.

Then, it is determined whether or not the motor 21 (the cutting tool) has stopped, that is, whether the rotational speed Rr is 0 or not (Step S149).

If it is determined in Step S149 that the rotational speed Rr is not 0 (if NO in Step S149), it means that the motor 21 has not stopped rotating yet, and thus the procedure returns to Step S147 to decrease the rotational speed Rr. In this way, the rotational speed Rr of the motor 21 is gradually decreased until the motor 21 stops rotating.

If it is determined in Step S149 that the rotational speed Rr is 0 (zero) (if YES in Step S149), the procedure returns to Step S101, and the motor 21 rotates in the forward direction.

According to this embodiment, the feedback control is performed so that the limit torque T1 is not exceeded as described above. As a result, the cutting tool can be prevented from being broken, and even if the cutting tool is jammed into a root canal, the motor can be rotated in the reverse direction to remove the cutting tool from the root canal, and after that, the motor can be rotated in the forward direction, so that the operation can be efficiently performed.

In addition, since the motor 21 is made to rotate in the reverse direction after the motor current Im decreases from the first limit current I1 to the second limit current I2, a torque drop can be reduced when the motor 21 is made to rotate in the reverse direction.

The second limit rotational speed R2 has been described as being set at the rotational speed Rr under the no-load condition in this embodiment. However, the second limit rotational speed R2 does not have to be exclusively set at the rotational speed Rr under the no-load condition, and if there is another empirically known value of the rotational speed Rr on which the determination of whether the cutting tool is removed from a root canal can be based, the second limit rotational speed R2 can also be set at the value.

<Control Characteristics of Reverse Mode>

Figure 5:
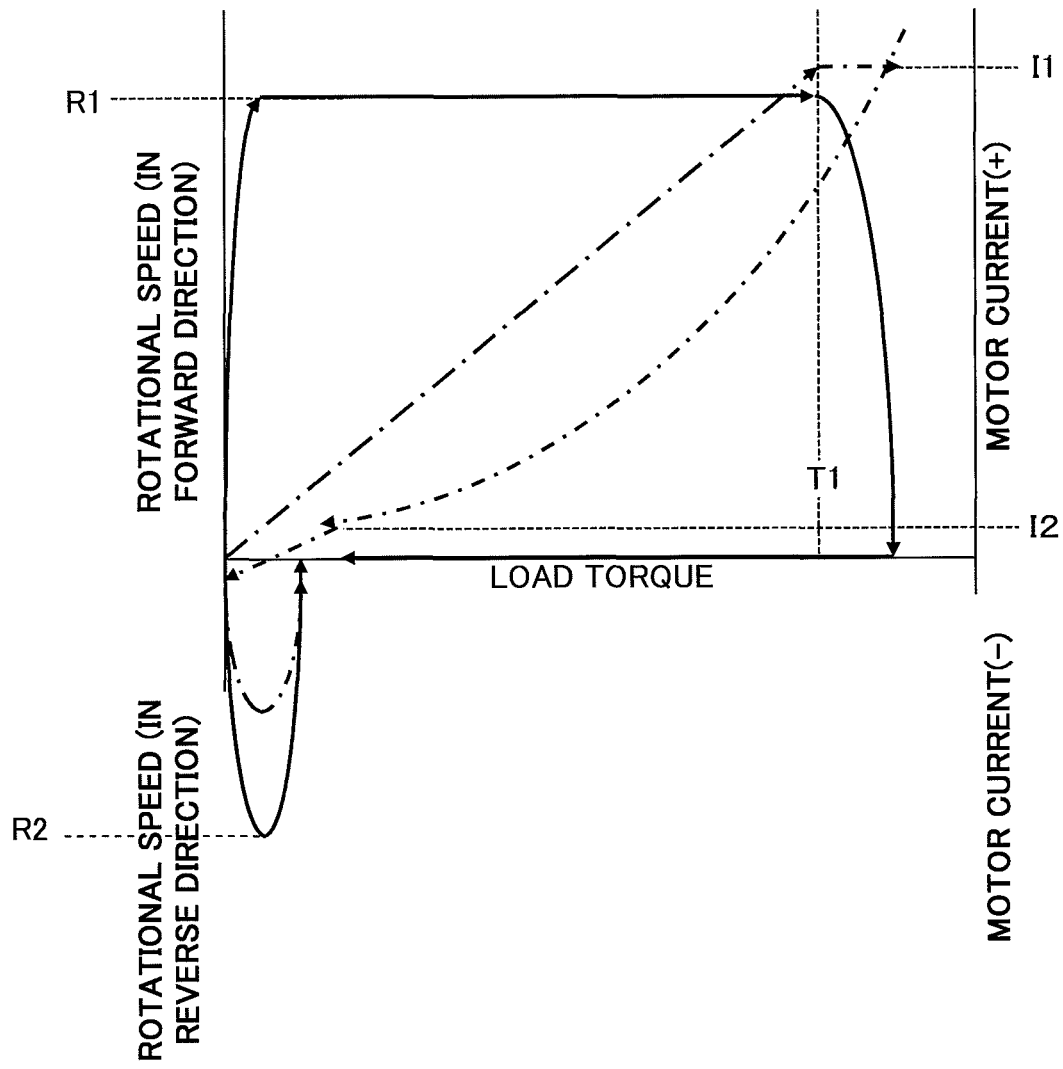
FIG. 5 is a control characteristics diagram of the load torque in the reverse mode of the motor control method according to the present invention.

FIG. 5 is a diagram showing control characteristics of the reverse mode according to this embodiment of the present invention shown in FIG. 4.

In FIG. 5, the control characteristics until the motor current Im reaches the second limit current I2 after the load torque Tr reaches the limit torque T1, and then the motor 21 stops rotating are the same as those of the stop mode, and therefore, the control characteristics after that will be described.

When the driving voltage Vd applied to the motor 21 is decreased, and the motor current Im decreases to the second limit current I2, the direction of the driving voltage Vd applied to the motor 21 is changed to make the motor 21 rotate in the reverse direction.

When the driving voltage Vd increases, and the rotational speed Rr of the motor 21 reaches the second limit rotational speed R2, the driving voltage Vd decreases until the motor current Im becomes 0. When the motor current Im becomes 0, the motor 21 starts rotating in the forward direction.

In this way, in the reverse mode, the cutting tool that has been jammed into a root canal and can hardly rotate is made to rotate in the reverse direction and then in the forward direction again. As a result, after the cutting tool is removed from the root canal, the operation can be resumed without any additional manipulations.

As described above, according to this embodiment of the present invention, the load torque is monitored during the feedback control, the cutting tool can be prevented from being broken, and the operation can be performed taking advantages of the feedback control that is superior in cutting efficiency.

In addition, the discomfort due to a torque drop can be reduced, since power supply to the motor 21 is stopped or the motor 21 is made to rotate in the reverse direction when the motor current Im decreases from the first limit current I1 to the second limit current I2 or lower.

Although the configuration according to this embodiment described above uses an external alternating-current power source, the present invention is not limited to this configuration and can also be applied to a cordless dental handpiece that incorporates a battery as a power source by inserting a circuit into the dental handpiece.

Furthermore, although the rotational speed of the motor 21 is controlled by the PWM driving scheme in this embodiment, the present invention is not limited to the scheme and can also adopt other driving schemes, such as the pulse amplitude modulation (PAM) driving scheme. In the case where the PAM driving scheme is used, a brush motor is used.

Furthermore, in the example described above, the motor 21 is made to rotate in the forward direction again after the motor 21 is made to rotate in the reverse direction in the reverse mode. However, as is apparent from the embodiment described above, the motor 21 can also be stopped after the motor 21 is made to rotate in the reverse direction.

The invention claimed is:

1. A motor control apparatus for a dental handpiece, the dental handpiece having a motor that rotationally drives a cutting tool, the motor control apparatus comprising:
   a load torque detecting section that detects a load torque applied to the cutting tool;
   a rotational speed detecting section that detects a rotational speed of the motor; and
   a control section that controls the rotational speed and a motor current of the motor,
   wherein the control section limits the motor current to a first limit current while the motor is energized, when the load torque detected by the load torque detecting section exceeds a preset limit torque value, wherein the first limit current is non-zero, and
   when the load torque exceeds the limit torque value and the rotational speed detecting section detects that the motor has stopped rotating while the motor is energized, gradually reduces the motor current over a period of time after the motor has stopped rotating and while the motor remains energized, to be equal to or lower than a second limit current, which is lower than the first limit current, and then stops power supply to the motor or makes the motor rotate in a reverse direction upon determining that the motor current becomes equal to or lower than the second limit current,
   wherein at an initial stage where the load torque applied to the cutting tool does not exceed the preset limit torque value, the motor control apparatus controls the rotational speed of the motor based on a feedback control so as to be set at a desired constant speed.

2. The motor control apparatus for a dental handpiece according to claim 1, wherein the control section stops power supply to the motor when the motor current becomes equal to or lower than the second limit current.

3. The motor control apparatus for a dental handpiece according to claim 1, wherein the control section makes the motor rotate in the reverse direction when the motor current becomes equal to or lower than the second limit current.

4. The motor control apparatus for a dental handpiece according to claim 1, wherein the control section makes the motor rotate in the reverse direction and then makes the motor rotate in a forward direction, which is the direction in which the motor rotates before the motor is made to rotate in the reverse direction, when the motor current becomes equal to or lower than the second limit current.

5. A motor control method for a dental handpiece, the dental handpiece having a motor that rotationally drives a cutting tool, the motor control method comprising:
   a step of controlling a rotational speed of the motor, at an initial stage where a load torque applied to the cutting tool does not exceed a preset limit torque value, based on a feedback control so as to be set at a desired constant speed;
   a step A of limiting a motor current, flowing through the motor while the motor is energized, to a first limit current when a load torque applied to the cutting tool exceeds a preset limit torque value, wherein the first limit current is non-zero; and
   when it is detected that the load torque exceeds the limit torque value and it is detected that the motor has stopped rotating, performing a step B of gradually reducing the motor current over a period of time after the motor has stopped rotating and while the motor remains energized, to be equal to or lower than a second limit current, which is lower than the first limit current, and then stopping power supply to the motor or making the motor rotate in a reverse direction upon determining that the motor current becomes equal to or lower than the second limit current, wherein the step A and the step B are performed by a motor control apparatus for controlling the motor.

6. The motor control method for a dental handpiece according to claim 5, wherein power supply to the motor is stopped when the motor current becomes equal to or lower than the second limit current in the step B.

7. The motor control method for a dental handpiece according to claim 5, wherein the motor is made to rotate in the reverse direction when the motor current becomes equal to or lower than the second limit current in the step B.

8. The motor control method for a dental handpiece according to claim 5, wherein the motor is made to rotate in a reverse direction and then made to rotate in the forward direction, which is the direction in which the motor rotates before the motor is made to rotate in the reverse direction, when the motor current becomes equal to or lower than the second limit current in the step B.

\* \* \* \* \*